US006821581B2

(12) United States Patent
Norisue et al.

(10) Patent No.: US 6,821,581 B2
(45) Date of Patent: Nov. 23, 2004

(54) OPTICALLY ACTIVE COMPOUND AND LIQUID CRYSTAL COMPOSITION CONTAINING THE COMPOUND

(75) Inventors: Yasumasa Norisue, Tokyo (JP); Yasue Ogi, Tokyo (JP); Masahiro Johno, Tokyo (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 44 days.

(21) Appl. No.: 10/178,233

(22) Filed: Jun. 25, 2002

(65) Prior Publication Data

US 2003/0124268 A1 Jul. 3, 2003

(30) Foreign Application Priority Data

Jun. 26, 2001 (JP) ....................................... 2001-192486

(51) Int. Cl.[7] ........................ C09K 19/20; C09K 19/12; C09K 19/32

(52) U.S. Cl. ............. 428/1.1; 252/299.64; 252/299.65; 252/299.67; 252/299.62

(58) Field of Search ....................... 252/249.01, 299.64, 252/255.65, 299.67, 299.62, 299.5; 428/1.1; 560/56

(56) References Cited

U.S. PATENT DOCUMENTS

| | | | | |
|---|---|---|---|---|
| 4,968,820 | A | 11/1990 | Scherowsky et al. | |
| 5,230,828 | A | 7/1993 | Kelly | |
| 6,217,792 | B1 | 4/2001 | Parri et al. | |
| 6,677,475 | B2 * | 1/2004 | Norisue et al. | 560/59 |

FOREIGN PATENT DOCUMENTS

| | | | |
|---|---|---|---|
| EP | 233602 | | 8/1987 |
| EP | 0 304738 | | 3/1989 |
| EP | 0 329153 | | 8/1989 |
| JP | 62-195347 | | 8/1987 |
| JP | 02-053768 | | 2/1990 |
| JP | 02 206678 | | 8/1990 |
| JP | 5-4944 | * | 1/1993 |
| JP | 05 017405 | | 1/1993 |
| JP | 05 025085 | | 2/1993 |

OTHER PUBLICATIONS

English translation by computer for JP 5–4944, http://www4.ipdl.jpo.go.jp/Tokujitu/PAJdetail.ipdl?N000=60&N0120=01&N2001=2&N3001=H05–004944.*

English translatipon by computer for JP 05–25085, http://www6.ipdl.jpo.go.jp/Tokujitu/PAJdetail.ipdl?N0000=80&N0120=01&N2001=2&N3001=H05–025085.*

Nakauchi, J., et al. "Ferroelectric liquid crystal mixtures doped with compounds having chiral groups at both ends of the core." Japanese Journal of Applied Physics, vol. 28, No 2. pp. L272–274, Feb. 1, 1989.

* cited by examiner

*Primary Examiner*—Shean C. Wu
(74) *Attorney, Agent, or Firm*—Sherman & Shalloway

(57) ABSTRACT

An optically active compound of the general formula (1) useful as a chiral dopant and use thereof, (1)

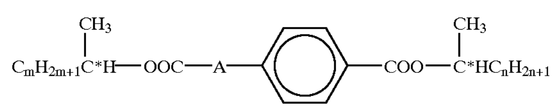

wherein each of m and n is independently an integer of 4 to 8, A is —Ph—COO—Ph—, —Ph—Ph—COO—, —Cy—COO—Ph—, —Ph—OOC—Ph—COO—, —Ph—OOC—Cy—COO—, —Ph—OOC—Np—COO— or —Np—OOC— in which —Ph— is a 1,4-phenylene group, —Cy— is a trans-1,4-cyclohexylene group and —Np— is a 2,6-naphtylene group, and C* is an asymmetric carbon atom.

Having a helical twisting power (HTP) of at least 9 and having a property that the helical pitch induced decreases with an increase in temperature, the optically active compound of the present invention has an excellent value as a chiral dopant for a nematic liquid crystal.

9 Claims, 1 Drawing Sheet

OPTICALLY ACTIVE COMPOUND AND LIQUID CRYSTAL COMPOSITION CONTAINING THE COMPOUND

DETAILED DESCRIPTION OF THE INVENTION

1. Field of the Invention

The present invention relates to a novel optically active compound useful as a chiral dopant, a liquid crystal composition containing the compound and a liquid crystal display device to which the liquid crystal composition is applied. More specifically, it relates to a chiral dopant having a helical twisting power (HTP) of at least 9 and having the property that a helical pitch induced by the chiral dopant decreases with an increase in temperature, and use thereof.

2. Prior Art

Various modes are known as display modes of liquid crystal display devices, and in most of such display modes, it is required to control the helical pitch of a liquid crystal. The mode that requires control of the helical pitch of a liquid crystal includes the following modes.

The modes that have been put to practical use and widely employed are a twisted nematic mode (TN mode) and a super twisted nematic mode (STN mode) using a nematic liquid crystal.

In the TN mode, liquid crystal molecules are aligned so as to twist at 90 degrees between an upper substrate and a lower substrate, and a ¼ pitch of a helix is formed in a cell.

In the STN mode, liquid crystal molecules are aligned so as to twist at approximately 220 degrees between an upper substrate and a lower substrate, and an approximately ⅗ pitch of a helix is formed in a cell.

The TN mode is employed in a simple matrix driving liquid crystal display device and an active matrix driving liquid crystal display device, and the STN mode is employed in a simple matrix driving liquid crystal display device.

BRIEF DESCRIPTION OF DRAWINGS

As another mode in addition to the above TN mode and STN mode, there is a selective reflection (SR) mode of a chiral nematic liquid crystal. As shown in FIGS. 1 and 2, in the SR mode, a liquid crystal has a planar state (FIG. 1) in which helical axes are perpendicular to substrates and a focal-conic state (FIG. 2) in which directions of helical axes are at random. These two states are switched with voltage pulse. In the planar state, light having a wavelength corresponding to a helical pitch is reflected, and in the focal-conic state, light is transmitted through a device. When a reflection state is used as "bright" and when a transmission state is used as "dark", a display is made possible.

Figure 1:
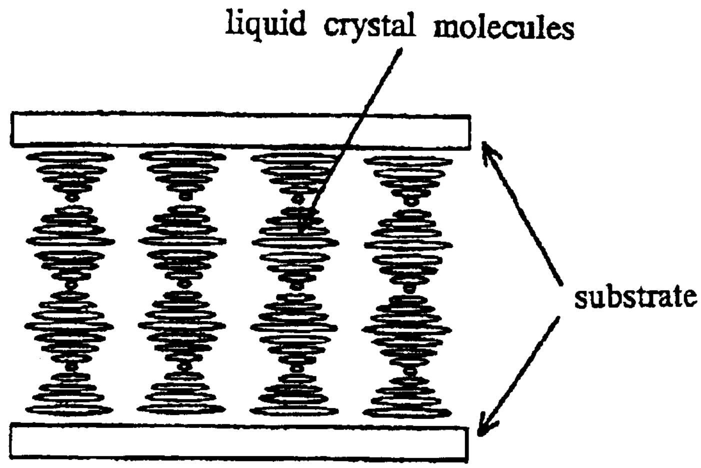
FIG. 1 schematically shows a planar alignment of a chiral nematic liquid crystal.
Figure 2:
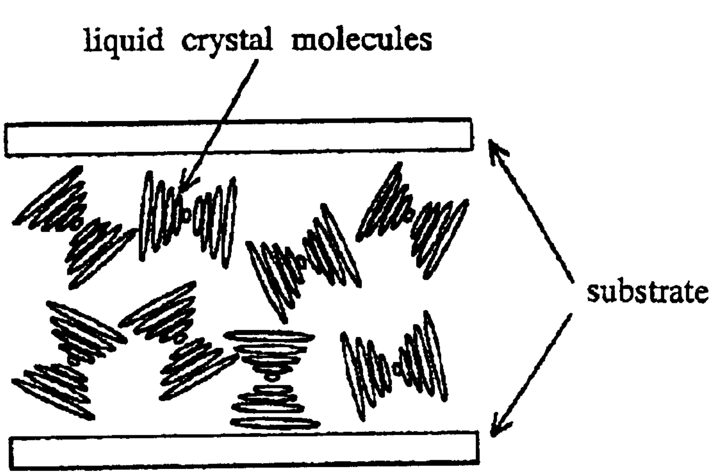
FIG. 2 schematically shows a focal-conic alignment of a chiral nematic liquid crystal.

In the present specification, "nematic liquid crystal" refers to a nematic liquid crystal that does not contain the chiral dopant of the present invention. Further, "liquid crystal composition" or "nematic liquid crystal composition" refers to a nematic liquid crystal composition containing the chiral dopant of the present invention. Further, "liquid crystal" refers to a composition containing a mixture of a plurality of liquid crystal compounds unless it is specified to be any specific compound, and the "liquid crystal" will be sometimes referred to as "base liquid crystal". Further, "chiral dopant" refers to an optically active compound that induces a helical structure or a mixture of such compounds.

As is already described, an optically active compound that induces a helical structure is generally called "chiral dopant". Many chiral dopants have been synthesized, and typical compounds thereof are compounds having the following structures.

| Name | Structural formula |
|---|---|
| S811; | 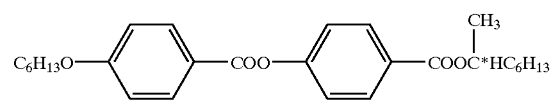 |
| CB15; | 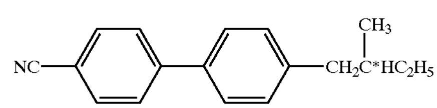 |
| CN; | 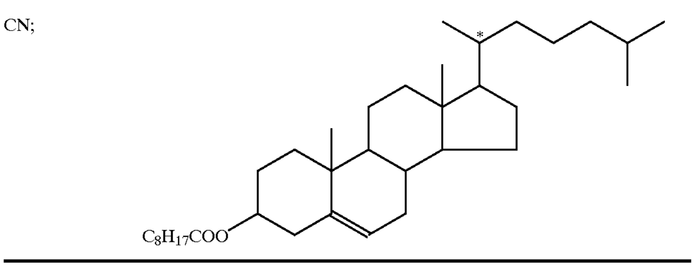 |

The most essential performance that is required of a chiral dopant compound is to have large helical twisting power. The helical twisting power (HTP) refers to a physical quantity defined by the following expression.

$$HTP(\mu m^{-1})=1/(\text{amount of chiral dopant added (wt \%)}/100\times\text{induced helical pitch } (\mu m))$$

Generally, chiral dopants themselves exhibit no liquid crystallinity, and most of them have large molecular weights. When a large amount of a chiral dopant is added to a base liquid crystal, it degrades various performances in many cases. The degradation of the performances includes a decrease in temperature for phase transition from an isotropic phase to a nematic phase, an increase in viscosity of a liquid crystal and an easy occurrence of crystallization. A chiral dopant having large helical twisting power serves to prevent the degradation of the performances since a desired helical pitch can be obtained by adding a small amount of such a chiral dopant to the base liquid crystal.

In addition to the above problems, the SR mode further has a problem that the helical pitch depends upon temperatures. That is, in the SR mode, a liquid crystal reflects (selectively reflects) light corresponding to a helical pitch to produce a bright state. However, when chiral dopants that have been already developed are used, the helical pitch increases in length with an increase in temperature, so that there is caused a problem that reflected light changes in color.

A change in wavelength of selectively reflected light with an increase in temperature is referred to as "wavelength shift". An increase in wavelength of selectively reflected light caused by an increase in temperature is defined to be plus wavelength shift, and a decrease in wavelength of selectively reflected light is defined to be minus wavelength shift.

For removing the dependency of wavelength of selectively reflected light upon temperatures, it has been attempted to combine a chiral dopant that shows a plus wavelength shift and a chiral dopant that shows a minus wavelength shift. However, there are very few chiral dopants that show a minus wavelength shift, and there are reported only four chiral dopants having a helical twisting power (HTP) of at least 9, which are disclosed in U.S. Pat. No. 6,217,792, JP-A-62-195347 and JP-A-2-053768. Those compounds that have been so far disclosed are not satisfactory, since these compounds exhibit small shift amounts and have a problem that they are liable to cause crystallization even when added in a small amount.

Problems to be Solved by the Invention

It is an object of the present invention to provide a chiral dopant that has large helical twisting power (HTP), as large as 9, and has a characteristic feature that the helical pitch induced decreases in length with an increase in temperature (has a minus wavelength shift).

Means to Solve the Problems

According to the present invention, there is provided an optically active compound of the following general formula (1) useful as a chiral dopant.

(1)

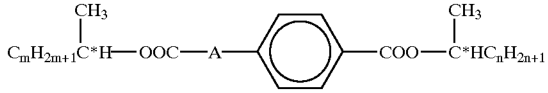

wherein each of m and n is independently an integer of 4 to 8, A is —Ph—COO—Ph—, —Ph—Ph—COO—, —Cy—COO—Ph—, —Ph—OOC—Ph—COO—, —Ph—OOC—Cy—COO—, —Ph—OOC—Np—COO— or —Np—OOC— in which —Ph— is a 1,4-phenylene group, —Cy— is a trans-1,4-cyclohexylene group and —Np— is a 2,6-naphtylene group, and C* is an asymmetric carbon atom.

The optically active compound of the above general formula (1) has excellent properties as a chiral dopant. The optically active compound of the present invention is accordingly used as an additive to nematic liquid crystals. That is, the optically active compound is used as a component for a nematic liquid crystal composition containing at least one compound thereof.

The nematic liquid crystal composition is held between substrates having electrodes and used for liquid crystal display devices.

In the above general formula (1), each of m and n is independently an integer of 4 to 8, preferably 5 to 7 and most preferably, each of m and n is 7. A is —Ph—COO—Ph—, —Ph—Ph—COO—, —Cy—COO—Ph—, —Ph—OOC—Ph—COO—, —Ph—OOC—Cy—COO—, —Ph—OOC—Np—COO— or —Np—OOC—, preferably —Ph—Ph—COO—, —Ph—COO— Ph—or —Ph—OOC—Np—COO—, and most preferably, it is —Ph—Ph—COO— or —Ph—COO—Ph—. The optically active compound of the above general formula (1) advantageously has a helical twisting power (HTP) of at least 9, more advantageously at least 10. Preferably, the optically active compound of the general formula (1) has a property that the helical pitch induced decreases in length with an increase in temperature.

The optically active compound of the present invention has two optically active carbon atoms on left and right hand sides, one each as shown in the general formula (1). The optically active compound therefore includes four optical isomers of R—R, R—S, S—R and S—S configurations according to optical active carbon.

Of the above optical isomers, the R—R and S—S configuration isomers have excellent properties as chiral dopants. The R—R configuration isomer and the S—S configuration isomer differ from each other in twisting direction (right-twisting or left-twisting) of the helical structure induced. When the compound of the general formula (1) are used, it is therefore selected from these isomers by taking account of the twisting direction of a chiral dopant to be used in combination.

Further, when a large amount of a single isomer from the optically active compound of the present invention is added to a nematic liquid crystal as a base liquid crystal, the resultant composition having some combination may undergo crystallization at room temperature. However, the crystallization can be easily avoided by using other chiral dopant in combination.

When the optically active compound of the present invention is used as a chiral dopant, the amount of the optically active compound based on the nematic liquid crystal to which the optically active compound is added, is generally in the range of from 1 to 30% by weight, preferably from 1 to 20% by weight. The above amount ratio is preferably determined to be in the above range on the basis of values of helical twisting power (HTP) and crystallinity of the optically active compound and a type of a nematic liquid crystal.

Effect of the Invention

According to the present invention, there is provided a chiral dopant that has a helical twisting power (HTP) of at least 9 and has the property that the induced helical pitch decreases in length with an increase in temperature. In liquid crystals for use in TN mode or STN mode, therefore, the helical pitch can be adjusted only by adding a small amount of the chiral dopant of the present invention, so that the degradation of performances of a base liquid crystal can be suppressed. In a liquid crystal operated in SR mode, a chiral dopant that induces a plus wavelength shift and the optically active compound of the present invention are used in combination, whereby there can be obtained a liquid crystal composition free of a change that occurs in helical pitch depending upon temperatures.

EXAMPLES

The present invention will be further specifically explained with reference to Examples and Comparative Examples, while the present invention naturally shall not be limited thereto.

Example 1

(Formula (1): m=7, n=7, A=—Ph—Ph—COO— (E1)), Preparation of 4-((R)-1-methyloctyloxycarbonyl)phenyl-4'-((R)-1-methyloctyloxycarbonyl)biphenyl-4-carboxylate (1) Synthesis of 4-acetoxybenozyl chloride 100 Grams (0.56 mol) of 4-acetoxybenzoic acid was added to 400 g (3.4 mol) of thionyl chloride, and a mixture was refluxed under heat for 4 hours. Then, excess thionyl chloride was distilled off, and the reaction mixture was purified by distillation under reduced pressure (4 mmHg, 116° C.) to give 99 g (0.50 mol, yield 90%) of an end product.

(2) Synthesis of (R)-1-methyloctyl-4-acetoxyphenylcarboxylate

A reactor was charged with 7.3 g (37 mmol) of acetoxybenzoyl chloride, 5.3 g (37 mmol) of (R)-2-nonanol and 150 ml of dehydrated toluene, and 5.8 g (74 mmol) of pyridine was dropwise added. A mixture was stirred at room temperature for 7 hours.

Then, 100 ml of water was placed in the reactor, and the mixture was stirred at room temperature for 30 minutes. Then, a liquid of an organic layer was separated. The organic layer was washed with 2N hydrochloric acid, with 1N sodium hydroxide and with water. Then, the organic layer was dried over dehydrated sodium sulfate and then filtered, and the solvent was distilled off, to give 11 g (37 mmol, yield 99%) of an end product.

(3) Synthesis of (R)-1-methyloctyl-4-hydroxyphenylcarboxylate

A reactor was charged with 11 g (37 mmol) of (R)-1-methyloctyl-4-acetoxyphenylcarboxylate and 150 ml of dehydrated toluene, 5.7 g of a methanol solution containing 40% methylamine (73 mmol of methylamine) was dropwise added, and a mixture was stirred at room temperature for 6 hours.

A reaction solution was washed with 2N hydrochloric acid and with water, and dried over dehydrated sodium sulfate and then filtered, and the solvent was distilled off, to give 8.7 g (33 mmol, yield 89%) of an end product.

(4) Synthesis of 4-((R)-1-methyloctyloxycarbonyl)phenyl-4'-((R)-1-methyloctyloxycarbonyl)biphenyl-4-carboxylate A reactor was charged with 4 g (15 mmol) of (R)-1-methyloctyl-4-hydroxyphenylcarboxylate, 5.6 g (20 mmol) of 4,4'-biphenyldicarbonyl chloride and 200 ml of dehydrated toluene, and 3.2 g (40 mmol) of pyridine was added. The mixture was stirred at room temperature for 5 hours. To the mixture was further added 3.6 g (25 mmol) of (R)-2-nonanol, and the mixture was stirred at room temperature for 90 hours. To a reaction solution was added 100 ml of water, and a mixture was stirred at room temperature for 30 minutes. Then, a liquid of an organic layer was separated. The organic layer was washed with 2N hydrochloric acid, with 1N sodium hydroxide and with water, and dried over anhydrous sodium sulfate. The organic layer was filtered, and then the solvent was distilled off. The thus-obtained crude product was purified by silica gel column chromatography, to give 3.8 g (6.2 mmol, yield 42%) of an end product.

Examples 2–4

(Formula (1): m=4, n=4, A=—Ph—Ph—COO— (E2)), Preparation of 4-((R)-1-methylpentyloxycarbonyl)phenyl-4'-((R)-1-methylpentyloxycarbonyl)biphenyl-4-carboxylate, (Formula (1): m=5, n=5, A=—Ph—Ph—COO— (E3)), Preparation of 4-((R)-1-methylhexyloxycarbonyl)phenyl-4'-((R)-1-methylhexyloxycarbonyl)biphenyl-4-carboxylate, and (Formula (1): m=6, n=6, A=—Ph—Ph—COO— (E4)), Preparation of 4-((R)-1-methylheptyloxycarbonyl)phenyl-4'-((R)-1-methylheptyloxycarbonyl)biphenyl-4-carboxylate.

Example 1 was repeated except that the (R)-2-nonanol used in (2) and (4) of Example 1 was replaced with (R)-2-hexanol (Example 2), (R)-2-heptanol (Example 3) or (R)-2-octanol (Example 4).

Example 5

(Formula (1): m=7, n=7, A=—Ph—COO—Ph— (E5)), Preparation of 4-((R)-1-methyloctyloxycarbonyl)biphenyl-4'-((R)-1-methyloctyloxycarbonyl)benzoate (1) Synthesis of 4'-acetoxybiphenyl-4-carboxylic acid A reactor was charged with 50 g (234 mmol) of 4'-hydroxybiphenyl-4-carboxylic acid and 238 g (2.34 mol) of acetic anhydride, and while a mixture was stirred, 0.1 g of concentrated sulfuric acid was added. The mixture was stirred until heat generation ceased, and the mixture was further stirred under heat at 80° C. for 4 hours. Then, the mixture was gradually cooled to room temperature.

While the above mixture was cooled with an ice bath, 500 g of water was gradually added, a mixture was stirred at room temperature for 3 hours, and unreacted acetic anhydride was quenched. A precipitated white solid was recovered by filtration, washed with water to remove acetic acid and dried with a vacuum dryer, to give 59.8 g (yield 99%) of an end compound.

(2) Synthesis of 4'-acetoxybiphenyl-4-carbonyl chloride

A reactor was charged with 59.8 g (233.4 mmol) of 4'-acetoxybiphenyl-4-carboxylic acid and 278 g (2.33 mol) of purified thionyl chloride, and a mixture was refluxed under heat (79° C.) for 4 hours.

Thionyl chloride was distilled off under atmospheric pressure, 150 ml of toluene was added to a remainder, and toluene and thionyl chloride were distilled off under reduced pressure, to give 63 g (yield 98%) of an end compound.

(3) Synthesis of (R)-1-methyloctyl-4'-acetoxybiphenyl-4-carboxylate

A reactor was charged with 10 g (37 mmol) of 4'-acetoxybiphenyl-4-carbonyl chloride, 5.3 g (37 mmol) of (R)-2-nonanol and 150 ml of toluene, 5.8 g (74 mmol) of pyridine was dropwise added thereto, and a mixture was stirred at room temperature for 3 hours.

To a reaction solution was added 80 ml of water, a mixture was stirred at room temperature for 30 minutes, and a liquid of an organic layer was separated.

The organic layer was washed with 2N hydrochloric acid, with a 1N sodium hydroxide aqueous solution and with water, and the washed organic layer was dried over anhydrous sodium sulfate and filtered. Then, the solvent was distilled off, to give 14 g (36 mmol, yield 98%) of an end compound.

(4) Synthesis of (R)-1-methyloctyl-4'-hydroxybiphenyl-4-carboxylate

A reactor was charged with 14 g (36 mmol) of (R)-1-methyloctyl-4'-acetoxybiphenyl-4-carboxylate and 150 ml of toluene, 5.7 g of a methanol solution containing 40% methylamine (73 mmol % of methylamine) was dropwise added, and a mixture was stirred at room temperature for 3 hours.

A reaction solution was washed with 2N hydrochloric acid and with water, to separate the solution, and an organic layer was dried over anhydrous sodium sulfate and filtered. Then, the solvent was distilled off, to give 11 g (32 mmol, yield 90%) of an end compound.

(5) Synthesis of 4-((R)-1-methyloctyloxycarbonyl) biphenyl-4'-((R)-1-methyloctyloxycarbonyl)benzoate A reactor was charged with 3.0 g (8.8 mmol) of (R)-1-methyloctyl-4'-hydroxybiphenyl-4-carboxylate, 2.4 g (12 mmol) of terephthalyl dichloride and 110 ml of dehydrated toluene, 1.9 g (23 mmol) of pyridine was dropwise added, and a mixture was stirred at room temperature for 5 hours. To the mixture was further added 1.3 g (11 mmol) of (R)-2-nonanol, and the mixture was stirred at room temperature for 19 hours.

To the thus-obtained reaction solution was added 50 ml of water, and a mixture was stirred at room temperature for 30 minutes. Then, a liquid of an organic layer was separated. The organic layer was washed with 2N hydrochloric acid, with 1N sodium hydroxide and with water, and the washed organic layer was dried over anhydrous sodium sulfate. Then, the solvent was distilled off. The thus-obtained crude product was purified by silica gel chromatography and recrystallized from ethanol, to give 1.5 g (2.4 mmol, yield 27%) of an end compound.

Example 6

(Formula (1): m=7, n=7, A=—Ph—OOC—Np—COO—(E6)), Preparation of 2,6-bis[4-((R)-1-methyloctyloxycarbonyl)phenyloxycarbonyl]naphthalene A reactor was charged with 4.1 g (16 mmol) of (R)-1-methyloctyl-4-hydroxyphenylcarboxylate obtained by repeating Example 1 up to (3) of Example 1, 1.7 g (7.7 mmol) of 2,6-naphthalenedicarboxylic acid, 1.8 g (8.5 mmol) of N,N'-dicyclohexylcarbodiimide and 70 ml of dehydrated dicyclomethane, and 0.18 g (1.5 mmol) of 4-dimethylaminopyridine was added thereto. A mixture was stirred at room temperature for 72 hours.

A reaction solution was filtered, followed by washing with 2N hydrochloric acid, with 1N sodium hydroxide and with water. An organic layer was dried over anhydrous sodium sulfate and filtered, and the solvent was distilled off. The thus-obtained crude product was purified by silica gel chromatography, to give 1.2 g (1.7 mmol, yield 21%) of an end compound.

With regard to the optically active compounds (E1 to E6) obtained in the above Examples 1 to 6, a common portion in the structural formula and A' portions in the general formula are respectively shown below, and results of $^1$H-NMR thereof are also shown in Table 1.

TABLE 1

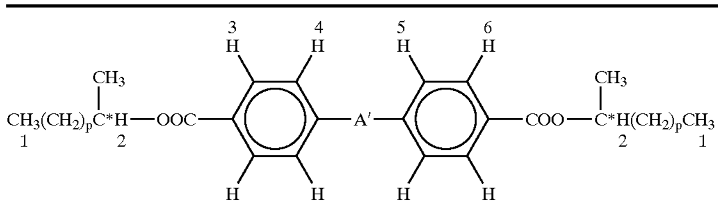

—A'— group;

[E1, E2, E3, E4]

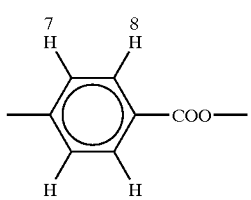

[E5]

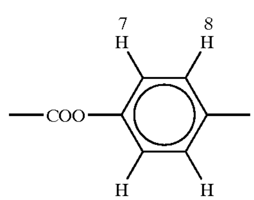

[E6]

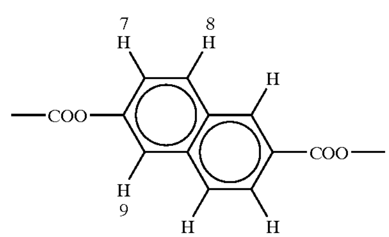

p = 6(E1), 3(E2), 4(E3), 5(E4), 6(E5), 6(E6)

$^1$H-NMR (δ, ppm)

| | Common portions | | | | | | A' portions | | |
|---|---|---|---|---|---|---|---|---|---|
| No. | 1 | 2 | 3 | 4 | 5 | 6 | 7 | 8 | 9 |
| E1 | 0.88 | 5.18 | 8.15 | 7.73 | 7.33 | 8.29 | 7.72 | 8.15 | — |
| E2 | 0.92 | 5.15 | 8.14 | 7.77 | 7.32 | 8.30 | 7.72 | 8.14 | — |
| E3 | 0.89 | 5.18 | 8.15 | 7.77 | 7.31 | 8.29 | 7.71 | 8.15 | — |
| E4 | 0.89 | 5.18 | 8.13 | 7.78 | 7.33 | 8.29 | 7.72 | 8.13 | — |
| E5 | 0.88 | 5.19 | 8.28 | 8.18 | 7.67 | 8.12 | 7.34 | 7.67 | — |
| E6 | 0.88 | 5.18 | 8.17 | 7.36 | 7.36 | 8.17 | 8.29 | 8.16 | 8.85 |

Further, phase transition temperatures of the optically active compounds (E1 to E6) were determined by observation through a polarizing microscope and DSC measurement. The results were as shown below.

| | |
|---|---|
| E1: Iso (21) Cry | E2: Iso (<−40) Cry |
| E3: Iso (22) Cry | E4: Iso (43) Cry |
| E5: Iso (21) Cry | E6: Iso (74) Cry |

In the above, parenthesized values refer to phase transition temperatures (° C.), Iso refers to an isotropic phase, and Cry refers to a crystalline phase.

Example 7

The optically active compounds (E1 to E6) prepared above were measured for helical twisting powers (HTP) and wavelength shifts.

To a nematic liquid crystal (ZLI-1565) supplied by Merck & Co., Inc., was added 15% by weight, based on a resultant composition, of the optically active compound (E1) obtained in Example 1, to prepare a chiral nematic (N*) liquid crystal composition.

The thus-prepared liquid crystal composition was measured for an upper limit temperature of its N* phase and selective reflection behaviors, and its helical twisting power (HTP) was determined on the basis of the selective reflection behaviors.

The upper-limit temperature of the N* phase was determined by observation through a polarizing microscope and DSC measurement.

The selective reflection behaviors were measured according to the following procedures.

A liquid crystal cell with ITO electrodes (cell thickness 10 μm) was charged with the above-prepared liquid crystal composition in an isotropic state. The cell was adjusted to 60° C., a rectangular wave voltage of ±60 V was applied for approximately 1 minute, and the cell was rapidly cooled to room temperature to attain planar alignment.

The above liquid crystal cell was evaluated for selective reflection behaviors at 25° C. and 60° C. with an automatic spectrophotometer. HTPs at 25° C. and 60° C. were calculated on the basis of the following expressions.

$$HTP(\mu m^{-1})=n/(\lambda_{25}\times C/100)$$

$$HTP(\mu m^{-1})=n/(\lambda_{60}\times C/100)$$

wherein n is a refractive index of the chiral nematic liquid crystal, $\lambda_{25}$ is a selective reflection wavelength (μm) at 25° C., $\lambda_{60}$ is a selective reflection wavelength (μm) at 60° C., and C is a concentration (wt %) of the chiral dopant. As a refractive index n, there was employed a value (1.6) that is the refractive index of ZLI-1565 as a base liquid crystal.

The wavelength shift was determined on the basis of the following expression.

Wavelength shift (nm)=$\lambda_{60}^*-\lambda_{25}^*$ wherein $\lambda_{60}^*$ is a selective reflection wavelength (nm) at 60° C. and $\lambda_{25}^*$ is a selective reflection wavelength (nm) at 25° C.

Talbe 2 shows the results.

The optically active compound (E1) of Example 1 had a large HTP of 9 or more and had a property that the helical pitch thereof decreased with an increase in temperature.

The optically active compounds (E2 to E6) obtained in Examples 2 to 6 were measured for HTPs and wavelength shifts in the same manner as above. Incidentally, with regard to the compound E2 alone, 10% by weight, based on a nematic liquid crystal composition, of the compound was added, and the composition was measured. Table 2 shows the results.

Comparative Examples 1–3

Those known optically active compounds CB15, S811 and CN shown in the explanation of Prior Art were measured for HTPs and wavelength shifts in the same manner as in Example 7.

For measurement of HTPs, CB15 and S811 were added in an amount of 15% by weight on the basis of a nematic liquid crystal to prepare nematic liquid crystal compositions, and CN was added in an amount of 30% by weight on the basis of a nematic liquid crystal to prepare nematic liquid crystal composition. These nematic liquid crystal compositions were measured for HTPs. Table 2 shows the results.

TABLE 2

| Compound | Iso-N*(° C.) | HTP(1/μm) | Wave length shift (nm) |
|---|---|---|---|
| E1 | 76 | 16.0 | −31 |
| E2 | 82 | 11.9 | −128 |
| E3 | 77 | 14.9 | −68 |
| E4 | 78 | 15.6 | −36 |
| E5 | 77 | 14.9 | −67 |
| E6 | 83 | 14.0 | −56 |
| CB15 | 74 | 7.9 | +193 |
| S811 | 73 | 10.1 | +7 |
| CN | 82 | 5.2 | +34 |

Notes) Iso-N* stands for a phase transition temperature (upper-limit temperature of N* phase) in a transition from an isotropric phase to a chiral nematic phase.

What is claimed is:

1. A nematic liquid crystal composition containing at least one of the optically active compound of the general formula (1) as chiral dopant, (1)

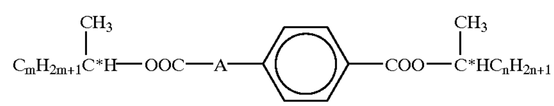

wherein each of m and n is independently an integer of 4 to 8, A is —Ph—COO—Ph—, —Ph—Ph—COO—, —Cy—COO—Ph—, —Ph—OOC—Ph—COO—, —Ph—OOC—Cy—COO—, —Ph—OOC—Np—COO— or —Np—OOC— in which —Ph— is a 1,4-phenylene group, and —Cy— is a 1,4-cyclohexylene group and —Np— is a 2,6-naphtylene group, and C* is an asymmetric carbon atom.

2. The nematic liquid crystal composition of claim 1, which the optically active compound has the general formula (1) wherein m and n are 5 to 7.

3. The nematic liquid crystal composition of claim 1, which the optically active compound has the general formula (1) wherein A is —Ph—COO—Ph—, —Ph—Ph—COO— or —Ph—OOC—Np—COO—.

4. The nematic liquid crystal composition of claim 1, which the optically active compound has the general formula (1) wherein A is —Ph—Ph—COO— or —Ph—COO—Ph—.

5. The nematic liquid crystal composition of claim 1, which the optically active compound has a helical twisting power, HTP, of at least 9.

6. The nematic liquid crystal composition of claim 1, which the optically active compound has a property that a helical pitch induced decreases in length with an increase in temperature.

7. The nematic liquid crystal composition of claim 1, which the optically active compound has the general formula (1) wherein two asymmetric carbon atoms together constitute R configurations or together constitute S configurations.

8. The nematic liquid crystal composition of claim 1, which the optically active compound contains in the range of from 1 to 30% by weight based on the composition.

9. A liquid crystal display device having the nematic liquid crystal composition recited in claim 1 interposed between substrates having an electrode each.

* * * * *